US010346984B2

(12) United States Patent
Hoi et al.

(10) Patent No.: US 10,346,984 B2
(45) Date of Patent: Jul. 9, 2019

(54) MEDICAL IMAGE PROCESSING APPARATUS, MEDICAL IMAGE PROCESSING METHOD, AND X-RAY CT APPARATUS

(71) Applicant: TOSHIBA MEDICAL SYSTEMS CORPORATION, Otawara-shi (JP)

(72) Inventors: Yiemeng Hoi, Vernon Hills, IL (US); Joseph Manak, Vernon Hills, IL (US); Kazumasa Arakita, Nasushiobara (JP); Jingwu Yao, Vernon Hills, IL (US); James Begelman, Vernon Hills, IL (US); Victor Gorin, Vernon Hills, IL (US)

(73) Assignee: Canon Medical Systems Corporation, Otawara-shi (JP)

( * ) Notice: Subject to any disclaimer, the term of this patent is extended or adjusted under 35 U.S.C. 154(b) by 0 days.

(21) Appl. No.: 16/032,363

(22) Filed: Jul. 11, 2018

(65) Prior Publication Data
US 2018/0330503 A1 Nov. 15, 2018

Related U.S. Application Data

(63) Continuation of application No. 15/360,135, filed on Nov. 23, 2016.

(51) Int. Cl.
| | |
|---|---|
| *G06K 9/00* | (2006.01) |
| *G06T 7/00* | (2017.01) |
| *A61B 6/03* | (2006.01) |
| *A61B 6/00* | (2006.01) |
| *G06T 17/20* | (2006.01) |

(52) U.S. Cl.
CPC ............ *G06T 7/0016* (2013.01); *A61B 6/032* (2013.01); *A61B 6/504* (2013.01); *A61B 6/5205* (2013.01);
(Continued)

(58) Field of Classification Search
CPC ................. G06T 7/0016; G06T 17/205; G06T 2207/10081; G06T 2207/20021;
(Continued)

(56) References Cited

U.S. PATENT DOCUMENTS 8,068,894 B2   11/2011  Huizenga et al.
9,687,212 B2*   6/2017  Hamada .................. A61B 8/06
(Continued)

FOREIGN PATENT DOCUMENTS

| JP | 2009-225850 | 10/2009 |
| JP | 2014-113264 | 6/2014 |
(Continued)

*Primary Examiner* — Shefali D Goradia
(74) *Attorney, Agent, or Firm* — Oblon, McClelland, Maier & Neustadt, L.L.P.

(57) ABSTRACT

A medical image processing apparatus according to an embodiment includes processing circuitry. The processing circuitry acquires image data including image data of a blood vessel of a subject. The processing circuitry performs analysis related to the blood vessel by using the image data, and specifies a region of interest in the blood vessel based on a result of the analysis. The processing circuitry performs fluid analysis on a region other than the region of interest at a first accuracy, and performs fluid analysis on the region of interest at a second accuracy that is higher than the first accuracy.

22 Claims, 9 Drawing Sheets

(52) U.S. Cl.
CPC .......... *A61B 6/5217* (2013.01); *G06T 17/205*
(2013.01); *G06T 2207/10081* (2013.01); *G06T
2207/20021* (2013.01); *G06T 2207/30104*
(2013.01)

(58) Field of Classification Search
CPC .......... G06T 2207/30104; A61B 6/032; A61B
6/504; A61B 6/5205; A61B 6/5217
See application file for complete search history.

(56) References Cited

U.S. PATENT DOCUMENTS

| | | |
|---|---|---|
| 10,159,418 B2 * | 12/2018 | Yamada ................ A61B 5/0261 |
| 2009/0238424 A1 | 9/2009 | Arakita et al. |
| 2013/0335083 A1 | 12/2013 | Wasserman |
| 2014/0249784 A1 | 9/2014 | Sankaran et al. |
| 2015/0032435 A1 | 1/2015 | Yagi et al. |
| 2015/0112191 A1 | 4/2015 | Gilboa et al. |
| 2015/0356734 A1 | 12/2015 | Ooga et al. |
| 2016/0128601 A1 | 5/2016 | Kennedy McConnell |
| 2016/0239958 A1 | 8/2016 | Bannae et al. |
| 2016/0310024 A1 | 10/2016 | Yoshida |

FOREIGN PATENT DOCUMENTS

| | | |
|---|---|---|
| JP | 2016-146995 | 8/2016 |
| WO | WO 2013/031743 A1 | 3/2013 |

\* cited by examiner

MEDICAL IMAGE PROCESSING APPARATUS, MEDICAL IMAGE PROCESSING METHOD, AND X-RAY CT APPARATUS

CROSS-REFERENCE TO RELATED APPLICATIONS

This application is a continuation Application of U.S. application Ser. No. 15/360,135, filed Nov. 23, 2016, the entire contents of which are incorporated herein by reference.

FIELD

Embodiments described herein relate generally to a medical image processing apparatus, a medical image processing method, and an X-ray CT apparatus.

BACKGROUND

In the conventionally known technology, fluid analysis on blood flow has been performed through simulation by using image data collected by a medical image diagnostic apparatus such as an X-ray computed tomography (CT) apparatus or a magnetic resonance imaging (MRI) apparatus.

DETAILED DESCRIPTION

A medical image processing apparatus according to an embodiment includes processing circuitry. The processing circuitry acquires image data including image data of a blood vessel of a subject. The processing circuitry performs analysis related to the blood vessel by using the image data, and specifies a region of interest in the blood vessel based on a result of the analysis. The processing circuitry performs fluid analysis on a region other than the region of interest at a first accuracy, and performs fluid analysis on the region of interest at a second accuracy that is higher than the first accuracy.

First Embodiment

Figure 1:
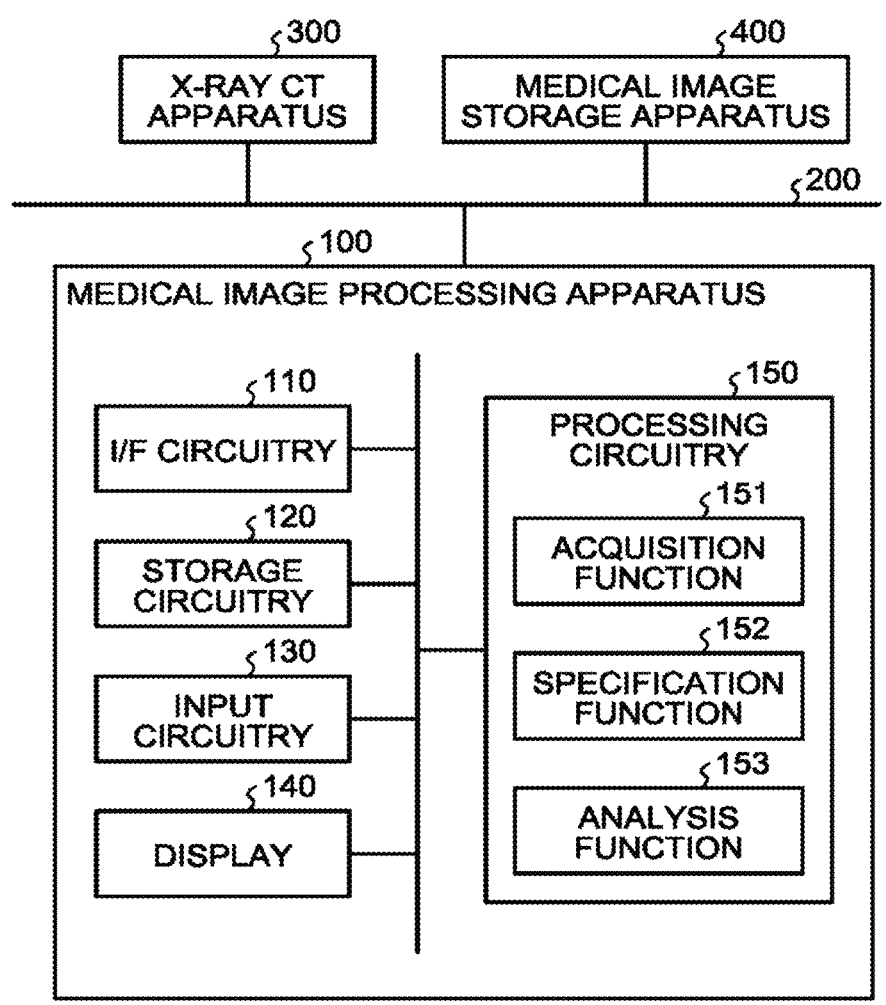
FIG. 1 is a diagram illustrating an exemplary configuration of a medical image processing apparatus according to a first embodiment.

FIG. 1 is a diagram illustrating an exemplary configuration of a medical image processing apparatus according to a first embodiment. For example, as illustrated in FIG. 1, this medical image processing apparatus 100 according to the present embodiment is mutually connected with an X-ray computed tomography (CT) apparatus 300 and a medical image storage apparatus 400 through a network 200 to perform communication therebetween. The medical image processing apparatus 100 may be additionally connected, through the network 200, with other medical image diagnostic apparatuses such as a magnetic resonance imaging (MRI) apparatus, an X-ray diagnostic apparatus, an ultrasonic diagnostic apparatus, and a positron emission tomography (PET) apparatus.

The X-ray CT apparatus 300 collects CT image data related to the subject. Specifically, the X-ray CT apparatus 300 rotates an X-ray tube and an X-ray detector around the subject substantially at a center, and collects projection data by detecting X-ray transmitted through the subject. Then, the X-ray CT apparatus 300 generates two-dimensional or three-dimensional CT image data based on the collected projection data.

The medical image storage apparatus 400 acquires the CT image data and the projection data from the X-ray CT apparatus 300 through the network 200, and stores the acquired CT image data and projection data in storage circuitry provided inside or outside of the apparatus. For example, the medical image storage apparatus 400 is achieved by a computer apparatus such as a server apparatus.

The medical image processing apparatus 100 acquires the CT image data from the X-ray CT apparatus 300 or the medical image storage apparatus 400 through the network 200, and performs various kinds of image processing on the acquired CT image data. The medical image processing apparatus 100 is achieved by a computer apparatus such as a work station.

For example, the medical image processing apparatus 100 includes interface (I/F) circuitry 110, storage circuitry 120, input circuitry 130, a display 140, and processing circuitry 150.

The I/F circuitry 110 is connected with the processing circuitry 150 and controls various data transmission and communication performed between the X-ray CT apparatus 300 and the medical image storage apparatus 400. In the present embodiment, the I/F circuitry 110 receives the CT image data from the X-ray CT apparatus 300 or the medical image storage apparatus 400, and outputs the received CT image data to the processing circuitry 150. For example, the I/F circuitry 110 is achieved by, for example, a network card, a network adapter, and a network interface controller (NIC).

The storage circuitry 120 is connected with the processing circuitry 150 and stores therein various kinds of data. In the present embodiment, the storage circuitry 120 stores therein the CT image data received from the X-ray CT apparatus 300 or the medical image storage apparatus 400. For example, the storage circuitry 120 is achieved by a semiconductor memory element such as a random access memory (RAM) or a flash memory, a hard disk, or an optical disk.

The input circuitry 130 is connected with the processing circuitry 150, converts an input operation received from an operator into an electric signal, and outputs the electric signal to the processing circuitry 150. For example, the input circuitry 130 is achieved by a track ball, a switch button, a mouse, a keyboard, or a touch panel.

The display 140 is connected with the processing circuitry 150 and displays thereon various kinds of information and various kinds of image data output from the processing circuitry 150. For example, the display 140 is achieved by a liquid crystal monitor, a cathode ray tube (CRT) monitor, or a touch panel.

The processing circuitry 150 controls each component included in the medical image processing apparatus 100 in accordance with an input operation received from the operator through the input circuitry 130. Specifically, the processing circuitry 150 stores the CT image data output from the I/F circuitry 110 in the storage circuitry 120. The processing circuitry 150 reads the CT image data from the storage circuitry 120 and displays the CT image data on the display 140. For example, the processing circuitry 150 is achieved by a processor.

The above description is made on the entire configuration of the medical image processing apparatus 100 according to the present embodiment. With such a configuration, the medical image processing apparatus 100 according to the present embodiment has a function that performs fluid analysis on blood flow through simulation by using the three-dimensional CT image data including image data of the blood vessel of the subject. For example, the medical image processing apparatus 100 according to the present embodiment is used in diagnosis or treatment of coronary artery stenosis.

Typically, the coronary artery stenosis includes a multifaceted problem, and thus, when reviewing the coronary artery stenosis, a multitude of information is needed. Simulation of the blood flow dynamics at the stenosis in fluid analysis can identify the severity of the stenosis. However, typically, an analysis result obtained by the simulation performed in fluid analysis tends to have a lower accuracy when the blood vessel has a complicated geometric shape or the blood flow exhibits a complicated pattern.

For this reason, the medical image processing apparatus 100 according to the present embodiment is configured to perform fluid analysis on the blood flow at a higher accuracy. The medical image processing apparatus 100 according to the present embodiment can be used in a similar manner in a case in which the target is a blood vessel in other organs such as a brain and a liver, as well as in the case in which a target of diagnosis or treatment is the coronary artery.

Specifically, in the medical image processing apparatus 100 according to the present embodiment, the processing circuitry 150 includes an acquisition function 151, a specification function 152, and an analysis function 153. The acquisition function 151 is an exemplary processing circuitry in the claims.

The acquisition function 151 acquires three-dimensional CT image data including image data of a blood vessel of the subject. Specifically, the acquisition function 151 acquires the CT image data from the X-ray CT apparatus 300 or the medical image storage apparatus 400, and stores the acquired CT image data in the storage circuitry 120.

The specification function 152 performs analysis related to the blood vessel by using the CT image data, and specifies a region of interest in the blood vessel of the subject based on a result of the analysis. Specifically, the specification function 152 reads, from the storage circuitry 120, the CT image data acquired by the acquisition function 151, and performs the analysis by using the read CT image data. Then, the specification function 152 specifies a region of interest in the blood vessel included in a CT image based on a result of the analysis.

The analysis function 153 performs fluid analysis on a region other than the region of interest at the first accuracy, and performs fluid analysis on the region of interest at the second accuracy that is higher than the first accuracy. Specifically, the analysis function 153 performs, based on the region of interest specified by the specification function 152, by using the CT image data acquired by the acquisition function 151, fluid analysis on the region other than the region of interest at the first accuracy, and fluid analysis on the region of interest at the second accuracy that is higher than the first accuracy.

In this manner, the medical image processing apparatus 100 according to the present embodiment specifies the region of interest in the blood vessel based on a result of the analysis related to the blood vessel, and performs fluid analysis on the specified region of interest at an accuracy that is higher than that for a region other than the region of interest. Accordingly, according to the present embodiment, fluid analysis on the blood flow can be performed at a higher accuracy.

Each processing function described above is stored in the storage circuitry 120, for example, as a computer-executable program. The processing circuitry 150 reads each computer program from the storage circuitry 120, and executes the read computer program to achieve the processing function corresponding to the computer program. In other words, having read the computer programs, the processing circuitry 150 includes the processing functions illustrated in FIG. 1.

Although FIG. 1 illustrates the example in which each processing function described above is achieved by the single processing circuitry 150, but the embodiment is not limited thereto. For example, the processing circuitry 150 may be configured as a combination of a plurality of independent processors such that each processor achieves each processing function by executing the corresponding computer program. The processing functions included in the processing circuitry 150 may be achieved through distribution or integration to a single processing circuitry or a plurality of processing circuitries as appropriate.

The following describes processing performed by the medical image processing apparatus 100 according to the present embodiment in more detail. The present embodiment describes an example in which the specification function 152 performs fluid analysis as the analysis related to the blood vessel.

Figure 2:
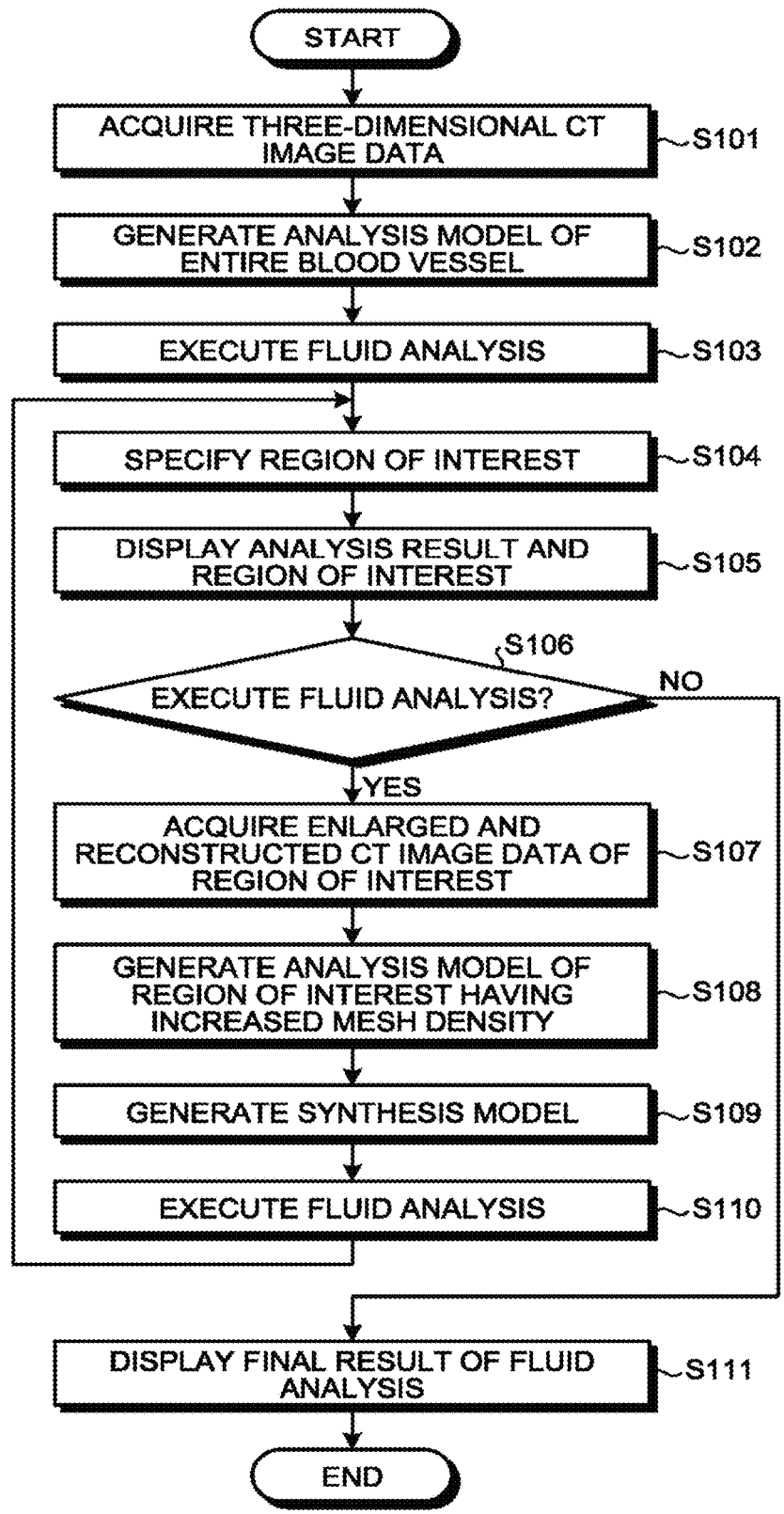
FIG. 2 is a flowchart of a processing procedure of fluid analysis performed by the medical image processing apparatus according to the first embodiment.

FIG. 2 is a flowchart of a processing procedure of fluid analysis performed by the medical image processing apparatus 100 according to the first embodiment.

For example, as illustrated in FIG. 2, in the present embodiment, first, the acquisition function 151 acquires three-dimensional CT image data including image data of a blood vessel of the subject from the X-ray CT apparatus 300 or the medical image storage apparatus 400 (step S101). Specifically, having received an operation instructing to start fluid analysis from the operator through the input circuitry 130, the acquisition function 151 acquires CT image data including image data of the blood vessel of the subject specified by the operator.

Subsequently, the specification function 152 executes fluid analysis by using the CT image data acquired by the acquisition function 151. Specifically, the specification function 152 performs fluid analysis on image data of the entire blood vessel included in the CT image data at a predetermined accuracy. The specification function 152 performs fluid analysis through simulation using a finite element method.

First, the specification function 152 generates an analysis model of the entire blood vessel included in the CT image data based on the CT image data at a predetermined accuracy (step S102).

Figure 3:
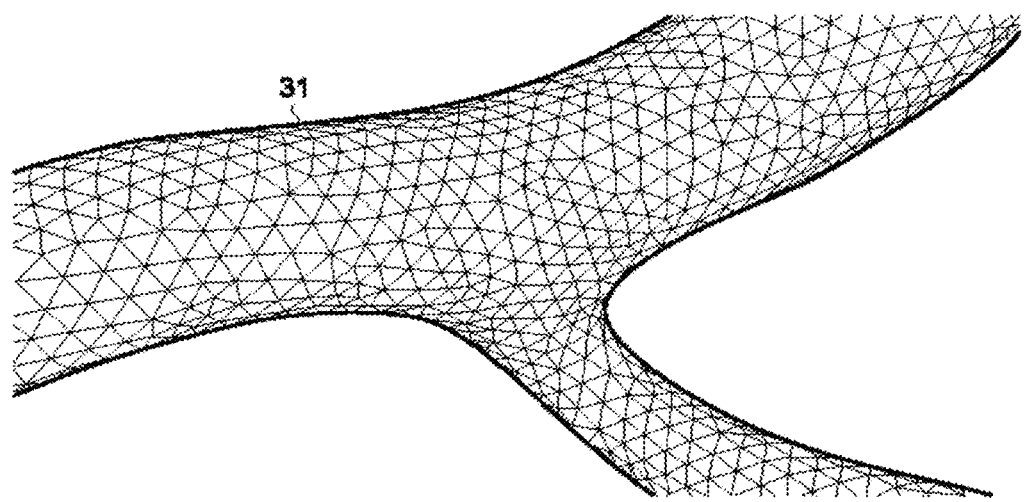
FIG. 3 is a diagram illustrating an exemplary analysis model generated by a specification function according to the first embodiment.

FIG. 3 is a diagram illustrating an exemplary analysis model generated by the specification function 152 according to the first embodiment. For example, as illustrated in FIG. 3, the specification function 152 generates an analysis model 31 of the blood vessel by dividing the shape of the blood vessel included in the CT image data into a mesh of a plurality of triangles. The specification function 152 sets the density of the mesh in the analysis model such that fluid analysis is performed at the predetermined accuracy described above.

Thereafter, the specification function 152 executes fluid analysis by using the generated analysis model (step S103). Specifically, the specification function 152 calculates a value of a blood flow parameter as a result of fluid analysis. The blood flow parameter is, for example, fractional flow reserve (FFR). The blood flow parameter may be various kinds of parameters other than the FFR. Examples of the blood flow parameter include blood flow velocity, velocity gradient, pressure, pressure gradient, pressure ratio, vorticity, kinetic energy, turbulence intensity, shear stress, and shear stress gradient.

Subsequently, the specification function 152 specifies a region of interest in the blood vessel of the subject based on the result of fluid analysis (step S104). Specifically, the specification function 152 specifies the region of interest to be a region in which the value of the blood flow parameter obtained as an analysis result through fluid analysis is out of a normal range. The normal range is determined in advance for each of the various kinds of parameters of the blood flow described above, and the range corresponding to the kind of the blood flow parameter used in analysis is used as appropriate.

Thereafter, the specification function 152 displays the result of fluid analysis and the region of interest on the display 140 (step S105). Then, the specification function 152 receives an operation to change the region of interest, and an operation to instruct whether to execute analysis on the region of interest from the operator through the input circuitry 130.

Figure 4:
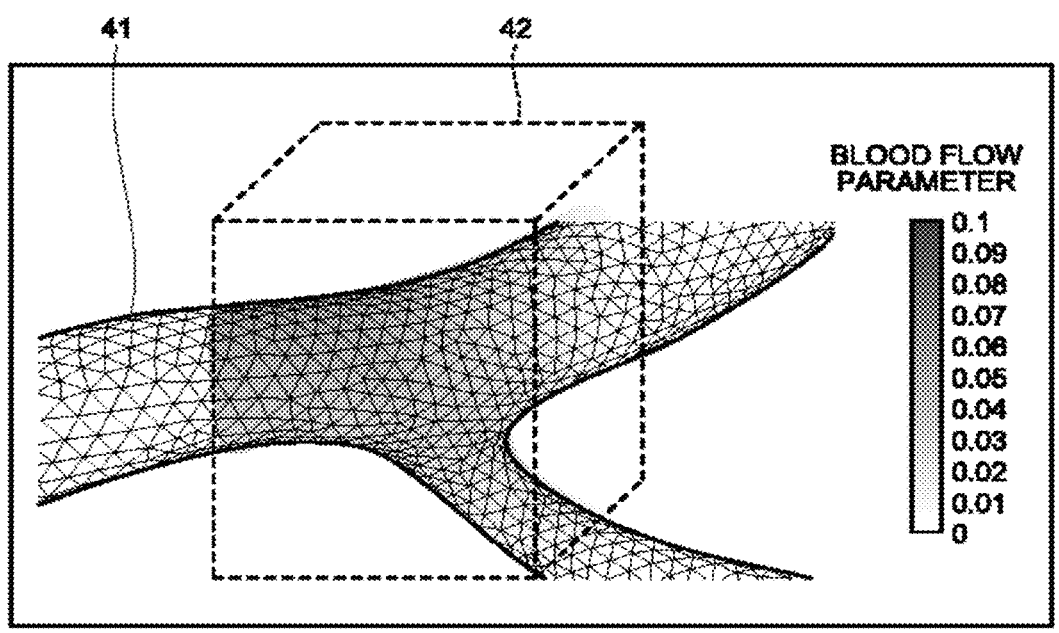
FIG. 4 is a diagram illustrating an exemplary analysis result and an exemplary region of interest displayed by the specification function according to the first embodiment.

FIG. 4 is a diagram illustrating an exemplary analysis result and an exemplary region of interest displayed by the specification function 152 according to the first embodiment. For example, as illustrated in FIG. 4, the specification function 152 displays, on the display 140, a graphic 41 illustrating the shape of an analysis model. Then, the specification function 152 displays, on the graphic 41 illustrating an analysis model, information indicating distribution of the value of the blood flow parameter obtained by fluid analysis. For example, the specification function 152 allocates different colors to values of the blood flow parameter, and colors the graphic 41 illustrating an analysis model in accordance with spatial distribution of the values of the blood flow parameter in the region of interest. The specification function 152 displays, on the graphic 41 illustrating an analysis model, a graphic 42 illustrating a specified range of the region of interest. When having received an operation to change the region of interest, the specification function 152 changes the range of the region of interest in accordance with the received operation, and displays, on the graphic 41 illustrating an analysis model, the graphic 42 illustrating the changed region of interest.

Then, if the specification function 152 has received an operation instructing execution of analysis on the region of interest (Yes at step S106), the analysis function 153 executes fluid analysis based on the region of interest being set at the time. Similarly to the specification function 152, the analysis function 153 performs fluid analysis through simulation using the finite element method.

In the first fluid analysis, the analysis function 153 performs fluid analysis on a region other than the region of interest at a predetermined accuracy same as that of fluid analysis performed by the specification function 152, and performs fluid analysis on the region of interest at an accuracy that is higher than the predetermined accuracy.

The analysis function 153 performs fluid analysis at an accuracy that is higher than the predetermined accuracy by increasing the resolution of image data as a basis of an analysis model used in fluid analysis. The analysis function 153 performs fluid analysis at an accuracy that is higher than the predetermined accuracy by increasing a calculation cost of fluid analysis. For example, the analysis function 153 increases the calculation cost of fluid analysis by increasing the density of the mesh in an analysis model by the finite element method.

Specifically, the analysis function 153 requests the X-ray CT apparatus 300 to reconstruct enlarged three-dimensional CT image data of a range in which the region of interest is being set at the time, and acquires the enlarged and reconstructed CT image data of the region of interest from the X-ray CT apparatus 300 (step S107). Accordingly, the CT image data of the region of interest having an increased resolution is obtained.

Subsequently, the analysis function 153 generates, based on the enlarged and reconstructed CT image data of the region of interest, an analysis model of the region of interest having an increased mesh density as compared with that in the analysis model used in the fluid analysis performed by the specification function 152 (step S108).

Instead of using the enlarged and reconstructed CT image data of the region of interest, the analysis function 153 may generate an analysis model of the region of interest having an increased mesh density obtained by setting a mesh finer than the mesh of the analysis model used in the fluid analysis performed by the specification function 152. This configuration eliminates the need to acquire the enlarged and reconstructed CT image data of the region of interest. In addition, with this configuration, after having generated an analysis model having a mesh with an increased density, the analysis function 153 may correct the mesh by comparing the generated analysis model with the CT image data.

Thereafter, the analysis function 153 generates a synthesis model obtained by coupling part of the analysis model of the entire blood vessel generated at the predetermined accuracy described above and corresponding to a part other than the region of interest, and the analysis model of the region of interest generated at an accuracy that is higher than the predetermined accuracy (step S109).

Figure 5:
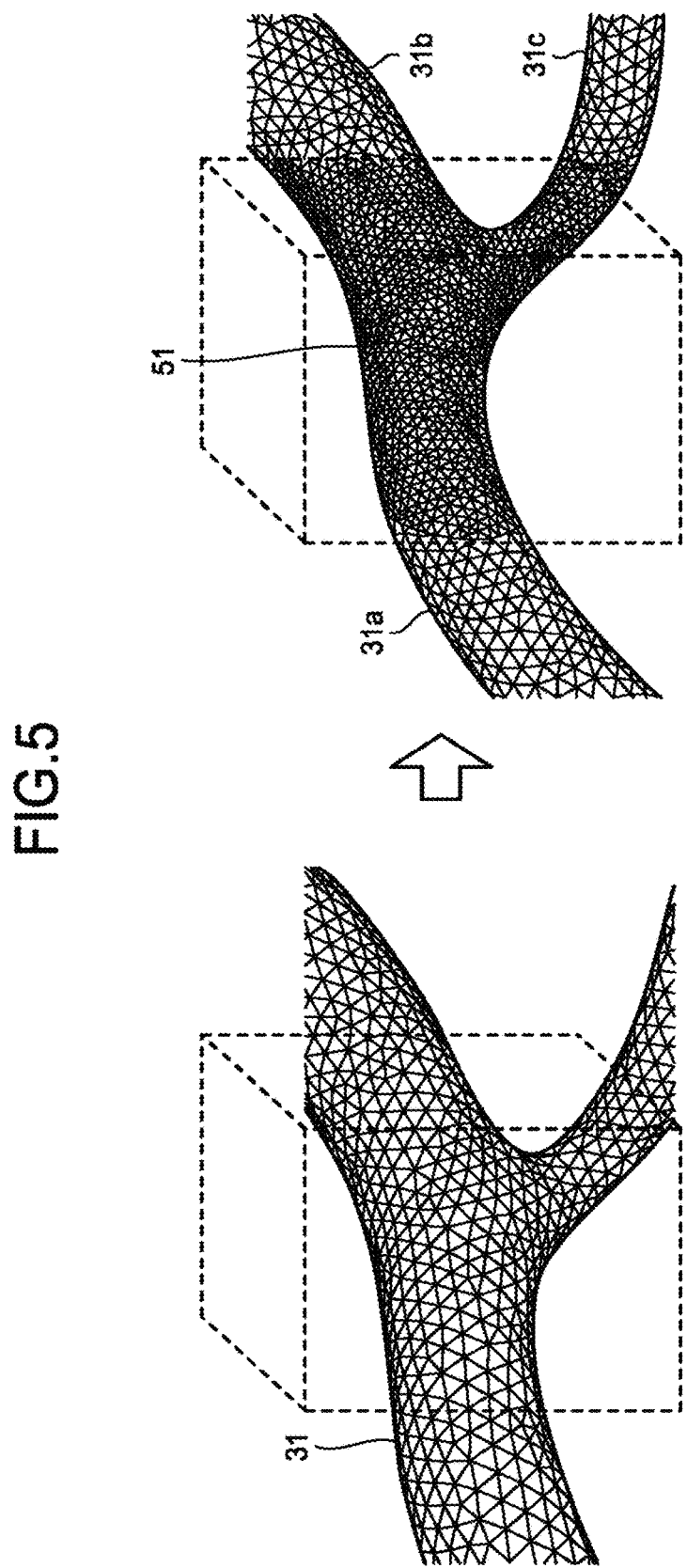
FIG. 5 is a diagram illustrating an exemplary synthesis model generated by an analysis function according to the first embodiment.

FIG. 5 is a diagram illustrating an exemplary synthesis model generated by the analysis function 153 according to the first embodiment. For example, as illustrated in FIG. 5, the analysis function 153 generates a synthesis model obtained by coupling parts 31a, 31b, and 31c of the analysis model 31 of the entire blood vessel, corresponding parts other than the region of interest, and an analysis model 51 of the region of interest. When such a synthesis model is used, fluid analysis is performed on the region of interest at an accuracy that is higher than that for a part other than the region of interest.

Then, the analysis function 153 executes fluid analysis on the entire blood vessel by using the generated synthesis model (step S110).

Thereafter, the specification function 152 specifies the region of interest again based on an analysis result obtained by newly performed fluid analysis (step S104), and displays a result of the fluid analysis and the region of interest on the display 140 (step S105).

Figure 6:
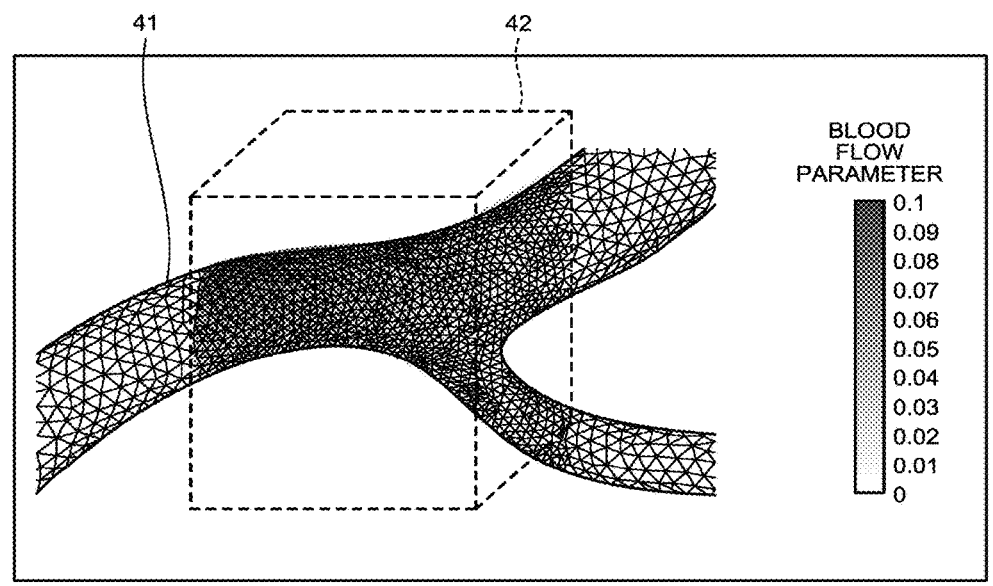
FIG. 6 is a diagram illustrating another exemplary analysis result and another exemplary region of interest displayed by the specification function according to the first embodiment.

FIG. 6 is a diagram illustrating another exemplary analysis result and another exemplary of the region of interest displayed by the specification function 152 according to the first embodiment. For example, similarly to the example illustrated in FIG. 4, as illustrated in FIG. 6, the specification function 152 displays the graphic 41 illustrating the shape of an analysis model, information indicating distribution of values of the blood flow parameter obtained by fluid analysis, and the graphic 42 illustrating a region of interest. The graphic 41 illustrating the shape of the analysis model is displayed based on a synthesis model used in the newly performed fluid analysis. The information indicating the distribution of values of the blood flow parameter is displayed based on the analysis result obtained by the newly performed fluid analysis. The graphic 42 illustrating the region of interest is displayed based on a previously set region of interest.

The operator can determine whether to execute fluid analysis again by referring to the result of fluid analysis displayed on the display 140. Then, if the specification function 152 has again received an operation instructing execution of analysis on the region of interest (Yes at step S106), the analysis function 153 executes fluid analysis again based on the region of interest being set at the time.

In the second and following fluid analysis, the analysis function 153 performs fluid analysis on the region other than the region of interest at an accuracy same as that in the previously performed fluid analysis, and performs fluid analysis on the region of interest at an accuracy that is higher than that in the previously performed fluid analysis.

In this case, the analysis function 153 performs fluid analysis at an accuracy that is higher than that of the previously performed fluid analysis by increasing the resolution of image data as a basis of an analysis model used in fluid analysis. The analysis function 153 also performs fluid analysis at an accuracy that is higher than that in the previously performed fluid analysis by increasing a calculation cost of fluid analysis. For example, the analysis function 153 increases the calculation cost of fluid analysis by increasing the density of a mesh in an analysis model by the finite element method.

Specifically, similarly to the first fluid analysis, the analysis function 153 acquires the enlarged and reconstructed CT image data of the region of interest from the X-ray CT apparatus 300 (step S107). Then, the analysis function 153 generates an analysis model of the region of interest having an increased mesh density as compared with that of an analysis model used in the previously performed fluid analysis by using the acquired CT image data (step S108).

Thereafter, the analysis function 153 generates a synthesis model obtained by coupling part of the analysis model of the entire blood vessel generated for the previously performed fluid analysis and corresponding to a part other than the region of interest, and the analysis model of the region of interest generated for new fluid analysis (step S109). Then, the analysis function 153 executes fluid analysis on the entire blood vessel by using the generated synthesis model (step S110).

In this manner, while the specification function 152 is receiving an operation instructing execution of analysis on the region of interest (Yes at step S106), the analysis function 153 repeats the execution of fluid analysis. Then, if the specification function 152 receives an operation instructing no execution of analysis on the region of interest (step S106, No), the analysis function 153 displays a result of previously performed fluid analysis as a final result on the display 140 (step S111).

Figure 7:
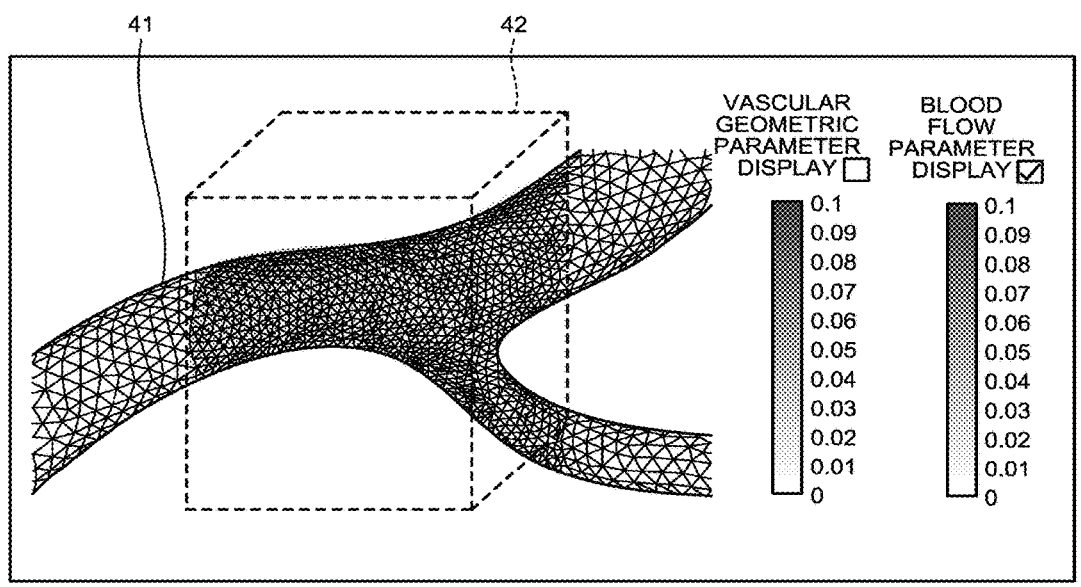
FIG. 7 is a diagram illustrating an exemplary final result displayed by the analysis function according to the first embodiment.

FIG. 7 is a diagram illustrating an exemplary final result displayed by the analysis function 153 according to the first embodiment. For example, as illustrated in FIG. 7, similarly to the examples illustrated in FIGS. 4 and 6, the analysis function 153 displays, as the final result, the graphic 41 illustrating the shape of an analysis model, information indicating distribution of values of the blood flow parameter obtained by fluid analysis, and the graphic 42 illustrating the region of interest. The graphic 41 illustrating the shape of an analysis model is displayed based on a synthesis model used in the previously performed fluid analysis. The information indicating the distribution of values of the blood flow parameter is displayed based on a result of the previously performed fluid analysis. The graphic 42 illustrating the region of interest is displayed based on the previously set region of interest.

In addition, for example, the analysis function 153 displays, as the final result, information indicating the value of a vascular geometric parameter related to an analysis model of the blood vessel. Examples of the vascular geometric parameters include, a blood vessel centerline, a coronary vessel lumen area, a coronary vessel diameter (size), a minimal luminal area, a minimal luminal diameter (size), the ratio of the minimal luminal area to the coronary vessel area, the ratio of the minimal luminal diameter to the coronary vessel size, a change of the coronary vessel lumen area along the vessel length, and the percentage of the coronary vessel lumen area to a pre-defined referenced area.

For example, similarly to the blood flow parameter, the specification function 152 allocates different colors to values of the vascular geometric parameter, and colors the graphic 41 illustrating an analysis model in accordance with spatial distribution of the values of the vascular geometric parameter in the region of interest.

For example, the specification function 152 receives, from the operator through the input circuitry 130, an operation to select display or non-display for each of information related to the blood flow parameter and information related to vascular geometric parameter. Then, the specification function 152 displays the information selected by the operator in accordance with the received operation on the graphic 41 illustrating an analysis model. For example, as illustrated in FIG. 7, the specification function 152 displays, on the display 140, a check box for selecting display or non-display for each of the blood flow parameter and vascular geometric parameter, and receives an operation to select display or non-display of each information from the operator.

Each step described above is achieved by, for example, the processing circuitry 150 loading the pre-defined computer program corresponding to each function from the storage circuitry 120 and executing the pre-defined computer program. Specifically, step S101 is achieved by, for example, the processing circuitry 150 loading the pre-defined computer program corresponding to the acquisition function 151 from the storage circuitry 120 and executing the pre-defined computer program. Steps S102 to S106 are achieved by, for example, the processing circuitry 150 loading the pre-defined computer program corresponding to the specification function 152 from the storage circuitry 120 and executing the pre-defined computer program. Steps S107 to S111 are achieved by, for example, the processing circuitry 150 loading the pre-defined computer program corresponding to the analysis function 153 from the storage circuitry 120 and executing the pre-defined computer program.

As described above, in the first embodiment, the medical image processing apparatus 100 specifies a region of interest in a blood vessel based on a result of fluid analysis, and performs fluid analysis on the specified region of interest at an accuracy that is higher than that in a region other than the region of interest. Accordingly, according to the present embodiment, fluid analysis on the blood flow can be performed at a higher accuracy.

The first embodiment described above may be modified as appropriate. The following describes a plurality of modifications of the first embodiment. The configuration of a medical image processing apparatus according to each modification is basically the same as the configuration illustrated in FIG. 1, and thus the following description is focused on any difference from the description in the first embodiment.

First Modification of First Embodiment

For example, the first embodiment above describes the example in which the specification function 152 performs fluid analysis as the analysis related to a blood vessel and specifies a region of interest in the blood vessel of the subject based on a result of this fluid analysis, but the present embodiment is not limited thereto. For example, the specification function 152 may perform image analysis as the analysis related to a blood vessel and specify a region of interest based on a result of this image analysis.

Figure 8:
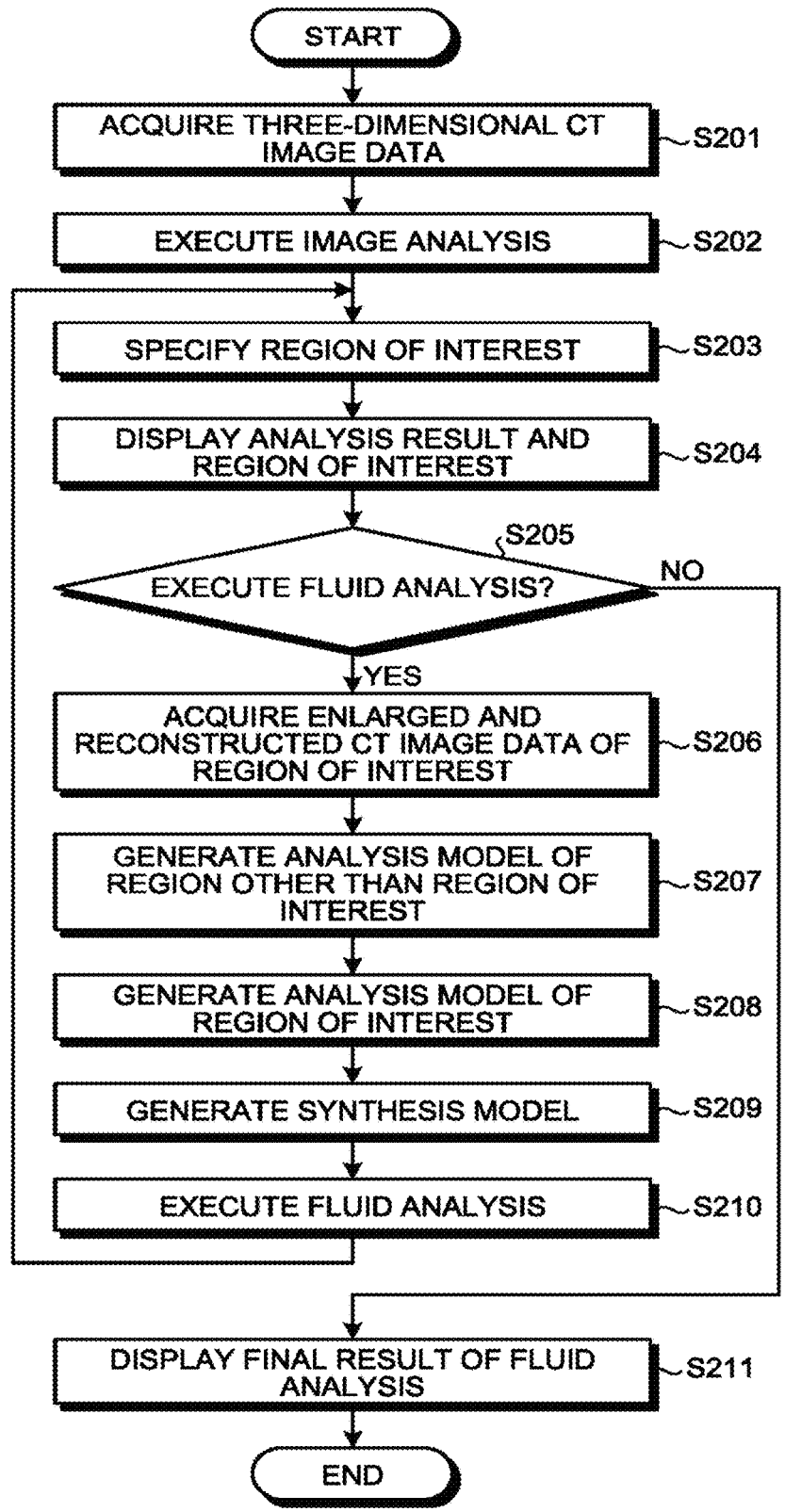
FIG. 8 is a flowchart of a processing procedure of fluid analysis performed by a medical image processing apparatus according to a first modification of the first embodiment.

FIG. 8 is a flowchart of processing procedure of fluid analysis performed by the medical image processing apparatus 100 according to a first modification of the first embodiment.

For example, as illustrated in FIG. 8, in the present modification, similarly to the first embodiment, the acquisition function 151 first acquires three-dimensional CT image data including image data of a blood vessel of the subject from the X-ray CT apparatus 300 or the medical image storage apparatus 400 (step S201).

Subsequently, the specification function 152 executes image analysis using the CT image data acquired by the acquisition function 151 (step S202). The specification function 152 specifies an abnormal region in the blood vessel by performing image analysis based on a pixel value included in the CT image data. Examples of the abnormal region specified by the specification function 152 include a region in which the amount of lesional tissue such as calcium exceeds a pre-defined amount, a region in which an artifact is present, and a region in which the blood vessel has a diameter smaller than a pre-defined threshold.

Subsequently, the specification function 152 specifies a region of interest in the blood vessel of the subject based on a result of the image analysis (step S203). For example, the specification function 152 specifies the region of interest to be the abnormal region obtained by the image analysis.

Thereafter, the specification function 152 displays the result of the image analysis and the region of interest on the display 140 (step S204). Similarly to the first embodiment, the specification function 152 receives, from the operator through the input circuitry 130, an operation to change the region of interest, and an operation to instruct whether to execute analysis on the region of interest.

For example, similarly to the example illustrated in FIG. 4, the specification function 152 displays, on the display 140, the graphic 41 illustrating the shape of an analysis model. Then, the specification function 152 displays, on the graphic 41 illustrating the analysis model, information indicating a region determined to be a lesion by the image analysis, and information indicating a region in which an artifact is determined to be present. For example, the specification function 152 colors, on the graphic 41 illustrating the analysis model, the region determined to be a lesion by the image analysis, and the region in which an artifact is determined to be present. The specification function 152 also displays, on the graphic 41 illustrating the analysis model, the graphic 42 illustrating the range of the specified region of interest. When having received an operation to change the region of interest, the specification function 152 changes the range of the region of interest in accordance with the received operation, and displays, on the graphic 41 illustrating the analysis model, the graphic 42 illustrating the changed region of interest.

Then, if the specification function 152 has received an operation instructing execution of analysis on the region of interest (Yes at step S205), the analysis function 153 executes fluid analysis based on the region of interest being set at the time. Similarly to the first embodiment, the analysis function 153 performs the fluid analysis through simulation using the finite element method.

In the first fluid analysis, the analysis function 153 performs fluid analysis on a region other than the region of interest at a pre-defined accuracy, and performs fluid analysis on the region of interest at an accuracy that is higher than the pre-defined accuracy.

In this case, the analysis function 153 performs fluid analysis at an accuracy that is higher than the pre-defined accuracy by increasing the resolution of image data as a basis of an analysis model used in fluid analysis. The analysis function 153 also performs fluid analysis at an accuracy that is higher than the pre-defined accuracy by increasing the calculation cost of fluid analysis. For example, the analysis function 153 increases the calculation cost of fluid analysis by increasing the density of a mesh in an analysis model by the finite element method.

Specifically, similarly to the first embodiment, the analysis function 153 requests the X-ray CT apparatus 300 to reconstruct enlarged three-dimensional CT image data of a range in which the region of interest is being set at the time, and acquires the enlarged and reconstructed CT image data of the region of interest from the X-ray CT apparatus 300 (step S206).

Subsequently, the analysis function 153 generates, based on the CT image data used in the image analysis performed by the specification function 152, an analysis model of a region other than the region of interest in the blood vessel included in the CT image data at the pre-defined accuracy described above (step S207). In addition, the analysis function 153 generates, based on the enlarged and reconstructed CT image data of the region of interest, an analysis model of the region of interest having an increased mesh density as compared with that of the analysis model generated at the pre-defined accuracy described above (step S208).

Thereafter, the analysis function 153 generates a synthesis model obtained by coupling the analysis model of the region other than the region of interest generated at the pre-defined accuracy described above, and the analysis model of the region of interest generated at an accuracy that is higher than the pre-defined accuracy (step S209). When such a synthesis model is used, similarly to the first embodiment, fluid analysis is performed on the region of interest at an accuracy that is higher than that for a part other than the region of interest.

Then, the analysis function 153 executes fluid analysis on the entire blood vessel by using the generated synthesis model (step S210).

Thereafter, the specification function 152 specifies the region of interest again based on an analysis result obtained by the newly performed fluid analysis (step S203), and displays a result of fluid analysis and the region of interest on the display 140 (step S204).

Similarly to the first embodiment, the operator can determine whether to execute fluid analysis again by referring to the result of fluid analysis displayed on the display 140. Then, if the specification function 152 has again received an operation instructing execution of analysis on the region of interest (Yes at step S205), the analysis function 153 executes fluid analysis again based on the region of interest being set at the time.

In the second and the following fluid analysis, the analysis function 153 performs fluid analysis on the region other than the region of interest at an accuracy same as that in the previously performed fluid analysis, and performs fluid analysis on the region of interest at an accuracy that is higher than that in the previously performed fluid analysis.

In this case, the analysis function 153 performs fluid analysis at an accuracy that is higher than that of the previously performed fluid analysis by increasing the resolution of image data as a basis of an analysis model used in fluid analysis. The analysis function 153 also performs fluid analysis at an accuracy that is higher than that of the previously performed fluid analysis by increasing the calculation cost of fluid analysis. For example, the analysis function 153 increases the calculation cost of fluid analysis by increasing the density of a mesh in an analysis model by the finite element method.

Specifically, similarly to the first fluid analysis, the analysis function 153 acquires the enlarged and reconstructed CT image data of the region of interest from the X-ray CT apparatus 300 (step S206). Then, the analysis function 153 generates an analysis model of fluid analysis at the pre-defined accuracy described above for the region other than the region of interest in the blood vessel by using the CT image data used in the image analysis performed by the specification function 152 (step S207). The analysis function 153 also generates, by using the acquired CT image data, an analysis model of the region of interest having an increased mesh density as compared with that of the analysis model used in the previously performed fluid analysis (step S208).

Thereafter, the analysis function 153 generates a synthesis model obtained by coupling the analysis model of the region other than the region of interest generated at the pre-defined accuracy described above, and the analysis model of the region of interest generated at an accuracy that is higher than the pre-defined accuracy (step S209). Then, the analysis function 153 executes fluid analysis on the entire blood vessel by using the generated synthesis model (step S210).

In this manner, while the specification function 152 is receiving an operation instructing execution of analysis on the region of interest (Yes at step S205), the analysis function 153 repeats the execution of fluid analysis. Then, if the specification function 152 receives an operation instructing no execution of analysis on the region of interest (No at step S205), the analysis function 153 displays a result of the previously performed fluid analysis as a final result on the display 140 (step S211). For example, similarly to the example illustrated in FIG. 7, the analysis function 153 displays the final result.

Each step described above is achieved by, for example, the processing circuitry 150 loading the pre-defined computer program corresponding to each function from the storage circuitry 120 and executing the pre-defined computer program. Specifically, step S201 is achieved by, for example, the processing circuitry 150 loading the pre-defined computer program corresponding to the acquisition function 151 from the storage circuitry 120 and executing the pre-defined computer program. Steps S202 to S205 are achieved by, for example, the processing circuitry 150 loading the pre-defined computer program corresponding to the specification function 152 from the storage circuitry 120 and executing the pre-defined computer program. Steps S206 to S211 are achieved by, for example, the processing circuitry 150 loading the pre-defined computer program corresponding to the analysis function 153 from the storage circuitry 120 and executing the pre-defined computer program.

As described above, in the first modification of the first embodiment, the medical image processing apparatus 100 specifies a region of interest in a blood vessel based on a result of image analysis, and performs fluid analysis on the specified region of interest at an accuracy that is higher than that in a region other than the region of interest. Accordingly, according to the present modification, fluid analysis on the blood flow can be performed at a higher accuracy.

Second Modification of First Embodiment

The first modification above describes the example in which the specification function 152 automatically performs image analysis, but the present embodiment is not limited thereto. For example, the specification function 152 may include a function to perform blood vessel analysis in accordance with an operation received from the operator.

In the present modification, the specification function 152 performs, as the analysis related to a blood vessel, blood vessel analysis that analyzes the structure of the blood vessel in accordance with an operation received from the operator, and specifies a region of interest to be an abnormal region obtained as a result of the blood vessel analysis.

Specifically, the specification function 152 extracts information such as a blood vessel centerline, a blood vessel wall, and a bifurcated shape from the blood vessel visualized in the CT image data in accordance with the operation received from the operator, and identifies, for example, a region in which a stenosis is generated and a stenosis rate based on the extracted information.

For example, the specification function 152 identifies the stenosis rate of the blood vessel in accordance with an operation received from the operator, and specifies a region of interest to be a range in which the stenosis rate exceeds a pre-defined threshold. For example, the specification function 152 specifies the region of interest to be a region having a stenosis rate of 50% or larger.

Then, in the present modification, the analysis function 153 may start fluid analysis while the specification function 152 is performing specification of the region of interest. In this case, when the region of interest is specified by the specification function 152, the analysis function 153 uses a result of fluid analysis completed so far for a region other than the region of interest. Accordingly, a time taken for fluid analysis on the blood vessel can be reduced.

Third Modification of First Embodiment

The first embodiment and the modifications above each describe the example in which the analysis function 153 increases the calculation cost of fluid analysis by increasing the density of a mesh in an analysis model by the finite element method, but the present embodiment is not limited thereto.

For example, the analysis function 153 may increase the calculation cost of fluid analysis through change from one-dimensional analysis to three-dimensional analysis. Alternatively, the analysis function 153 may increase the calculation cost of fluid analysis by increasing the convergence number of iterative calculation performed in fluid analysis.

Fourth Modification of First Embodiment

In the first embodiment and the modifications described above, the analysis function 153 generates a synthesis model by coupling an analysis model related to a region other than the region of interest and an analysis model related to the region of interest, but the analysis function 153 may smoothly couple the analysis models by applying space interpolation where the analysis models are coupled with each other at the generation of a synthesis model.

Figure 9:
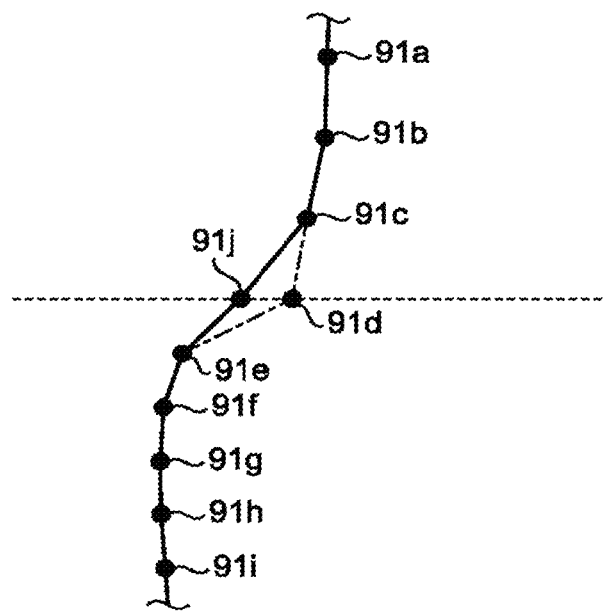
FIG. 9 is a diagram illustrating exemplary space interpolation of an analysis model performed by an analysis function according to a fourth modification of the first embodiment.

FIG. 9 is a diagram illustrating exemplary space interpolation of an analysis model performed by the analysis function 153 according to a fourth modification of the first embodiment. A plurality of points illustrated in FIG. 9 represent contact points of a mesh in an analysis model by the finite element method. Four contact points 91a to 91d illustrated in an upper side in FIG. 9 are contact points set in an analysis model related to the region other than the region of interest. Five contact points 91e to 91i illustrated in a lower side in FIG. 9 are contact points set in an analysis model related to the region of interest.

For example, as illustrated in FIG. 9, in the analysis model related to the region of interest, a finer mesh is set than that in the analysis model of the region other than the region of interest, and thus the contact points have shorter intervals therebetween. Thus, when a synthesis model is generated, the positions of contact points are shifted from each other where the analysis models are coupled due to, for example, a partial volume effect in some cases. For example, as illustrated in FIG. 9, a difference occurs between contact point 91d positioned in a coupled-side end part of the analysis model related to the region other than the region of interest, and contact point 91e positioned in a coupled-side end part of the analysis model related to the region of interest.

In such a case, the analysis function 153 smoothly couples the analysis models by applying space interpolation by using a method such as spline interpolation where the analysis models are coupled. For example, as illustrated in FIG. 9, the analysis function 153 interpolates, in place of contact point 91d positioned in the coupled-side end part of the analysis model related to the region other than the region of interest, new contact point 91j based on the positions of other contact points. In this manner, the analysis model related to the region of interest and the analysis model of the region other than the region of interest can be smoothly coupled, thereby achieving an improved accuracy of fluid analysis using a synthesis model.

Fifth Modification of First Embodiment

In the first embodiment and the modifications described above, the analysis function 153 performs fluid analysis using a synthesis model, but an analysis model used in the previously performed fluid analysis is used for a region upstream of the region of interest in the synthesis model, and thus fluid analysis provides a result same as the previously obtained result.

Thus, when performing fluid analysis using a synthesis model, the analysis function 153 may omit calculation in fluid analysis using an analysis result obtained by the previously performed fluid analysis for a region positioned upstream of the region of interest among regions other than the region of interest.

Figure 10:
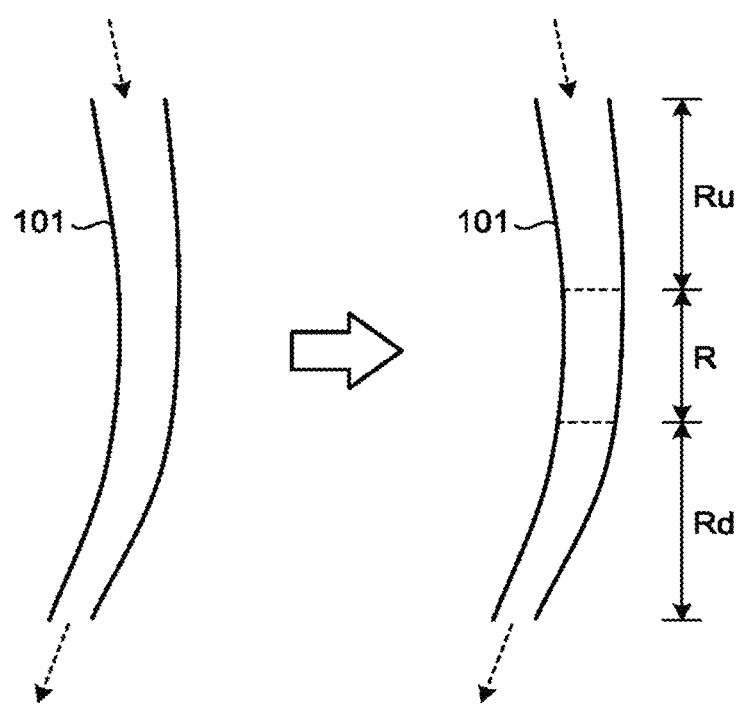
FIG. 10 is a diagram illustrating exemplary fluid analysis performed by an analysis function according to a fifth modification of the first embodiment.

FIG. 10 is a diagram illustrating exemplary fluid analysis performed by the analysis function 153 according to a fifth modification of the first embodiment. Diagrams illustrated on the left and right sides in FIG. 10 illustrate a synthesis model 101 of the entire blood vessel, and arrows with dashed lines illustrate the flow direction of the blood flow. In the diagram illustrated on the right side in FIG. 10, each range illustrated with a double-headed arrow illustrates the range of a region of interest R in the synthesis model 101.

For example, in the example illustrated in FIG. 10, the analysis function 153 omits calculation in fluid analysis using an analysis result obtained by the previously performed fluid analysis for a region Ru positioned upstream of the region of interest R among regions other than the region of interest R. The analysis function 153 also newly performs fluid analysis using the synthesis model 101 on the region of interest R and a region Rd positioned downstream of the region of interest R among regions other than the region of interest. Accordingly, a time taken for fluid analysis on the blood vessel can be reduced.

Sixth Modification of First Embodiment

In the first embodiment and the modifications described above, the specification function 152 displays a result of analysis related to a blood vessel on the display 140, but the specification function 152 may perform both of fluid analysis and image analysis and additionally display, based on a result of the image analysis, the reliability of an analysis result obtained by the fluid analysis.

Specifically, similarly to the first embodiment, the specification function 152 performs fluid analysis using the CT image data acquired by the acquisition function 151. Similarly to the first modification, the specification function 152 performs image analysis using the CT image data acquired by the acquisition function 151, and specifies an abnormal region in the blood vessel. For example, the specification function 152 specifies the abnormal region to be, for example, a region in which the amount of lesional tissue such as calcium exceeds a pre-defined amount, a region in which an artifact such as a motion artifact or a banding artifact is present, or a region in which the blood vessel has a diameter smaller than a pre-defined threshold.

Then, similarly to the first embodiment, the specification function 152 displays a result of fluid analysis and the region of interest on the display 140. In addition, the specification function 152 calculates the reliability of fluid analysis at each position in the blood vessel based on an analysis value obtained as a result of image analysis, and displays the calculated reliability together with the result of fluid analysis on the display 140.

For example, the specification function 152 calculates the reliability of fluid analysis at each position in the blood vessel based on the amount of lesional tissue such as calcium, the number of artifacts, and the coronary vessel diameter. Then, for example, as illustrated in FIG. 4, the specification function 152 displays, on the graphic 41 illustrating the shape of an analysis model, information indicating distribution of values of the blood flow parameter, and additionally displays information indicating the calculated reliability on the graphic 41. For example, the specification function 152 allocates different colors to values of the reliability, and colors the graphic 41 illustrating an analysis model in accordance with spatial distribution of the reliability in the blood vessel. Alternatively, the specification function 152 may display, on the graphic 41 illustrating an analysis model or near the graphic 41, a numerical value indicating the reliability. Accordingly, the operator can be presented with information to be referred to when determining whether to execute fluid analysis again.

Seventh Modification of First Embodiment

The specification function 152 may give notification of warning when the blood vessel includes a branch having a thickness larger than a pre-defined threshold and the reliability is lower than a pre-defined threshold in the region of the branch.

Figure 11:
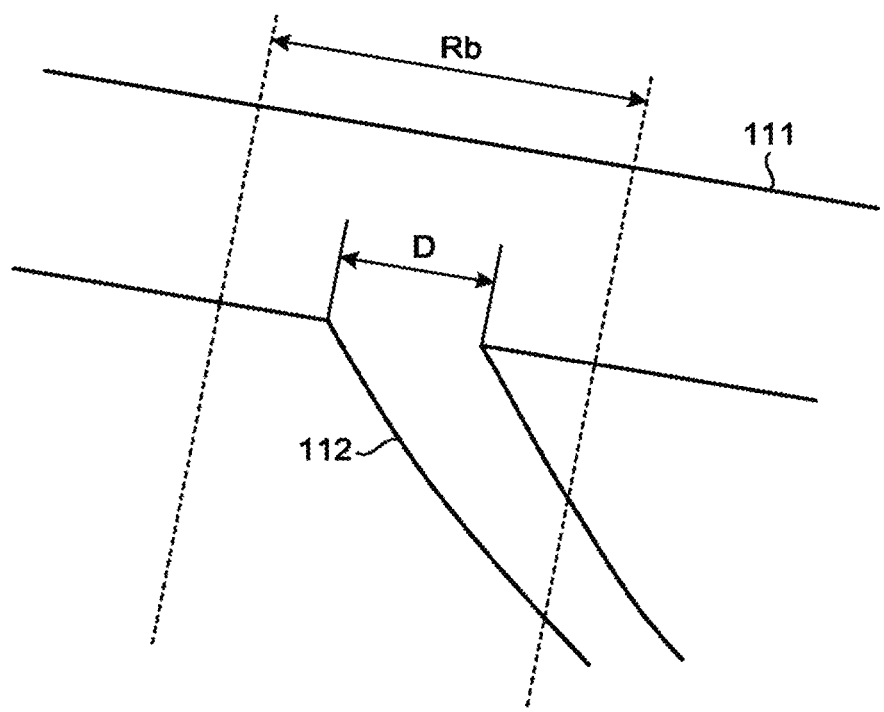
FIG. 11 is a diagram illustrating exemplary warning display related to a branch of a blood vessel performed by a specification function according to a seventh modification of the first embodiment.

FIG. 11 is a diagram illustrating exemplary warning display related to a branch of the blood vessel performed by the specification function 152 according to a seventh modification of the first embodiment. For example, as illustrated in FIG. 11, the specification function 152 detects a branch 112 that is a blood vessel bifurcating from a blood vessel 111 based on the CT image data acquired by the acquisition function 151, and calculates a coronary vessel diameter D of the branch 112 where the detected branch 112 and the blood vessel 111 connects with each other. Then, for example, when the calculated coronary vessel diameter D of branch 112 is 3 mm or larger, the acquisition function 151 detects whether there exists a region that includes a connected part between the blood vessel 111 and the branch 112 and in which the reliability of fluid analysis is lower than a pre-defined threshold. Then, if there exists such a region Rb, the acquisition function 151 displays, on the display 140, information indicating the region Rb and a warning message together with a result of fluid analysis.

Typically, in fluid analysis through simulation, when the blood vessel is finer or the blood vessel bifurcates, an analysis result has a lower accuracy in some cases. In other words, when the blood vessel is thick enough but the analysis result has a low reliability, it is likely that accurate fluid analysis has not been performed. In such a case, in the present modification, the operator can be prompted to perform fluid analysis again.

Eighth Modification of First Embodiment

The first embodiment and the modifications above describe the example in which an analysis model of the region of interest having an increased mesh density is generated based on the enlarged and reconstructed CT image data of the region of interest, but the present embodiment is not limited thereto. For example, instead of acquiring the enlarged and reconstructed CT image data of the region of interest, the analysis function 153 may perform image correction on the CT image data, and then perform fluid analysis at an improved accuracy by using the corrected image data.

In this case, instead of generating an analysis model of the region of interest having an increased mesh density based on the enlarged and reconstructed CT image data of the region of interest, the analysis function 153 performs image correction on the CT image data, and then generates, based on the corrected image data, an analysis model of the region of interest having an increased mesh density. For example, the analysis function 153 performs, on the CT image data, pre-defined image corrections such as motion artifact correction, banding artifact correction, and phase correction.

Ninth Modification of First Embodiment

Instead of performing the pre-defined image corrections as the image correction described above, the analysis function 153 may perform an image correction selected from among a plurality of kinds of image corrections. In this case, for example, the content of each image correction is stored in the storage circuitry 120 as a database in advance. Examples of the content of image correction include correction of a blood vessel wall, correction of a fake stenosis, and smoothing of pixel value change.

Then, for example, the analysis function 153 performs an image correction selected from the database by the operator. Alternatively, the analysis function 153 may automatically select an appropriate image correction from the database in accordance with results of image analysis and fluid analysis in accordance with a pattern associating an analysis result of the CT image data and the kind of an image correction in advance, and perform the selected image correction. Accordingly, the accuracy of fluid analysis can be increased.

Tenth Modification of First Embodiment

The first embodiment and the modifications described above describe the example in which the acquisition function 151 acquires the CT image data from the X-ray CT apparatus 300 or the medical image storage apparatus 400, but the present embodiment is not limited thereto. For example, instead of acquiring the CT image data, the acquisition function 151 may acquire projection data as a basis of the CT image data.

In this case, the acquisition function 151 acquires, from the X-ray CT apparatus 300 or the medical image storage apparatus 400, projection data as a basis of three-dimensional CT image data including image data of a blood vessel of the subject, and stores the acquired projection data in the storage circuitry 120. Then, when performing analysis related to a blood vessel, the specification function 152 and the analysis function 153 read the projection data from the storage circuitry 120, and reconstruct, or reconstruct in an enlarged manner, CT image data used in analysis from the read projection data.

Alternatively, similarly to the first embodiment, the acquisition function 151 may acquire CT image data, and the specification function 152 and the analysis function 153 may read the CT image data from the storage circuitry 120 and use the read CT image data to generate CT image data used in analysis. For example, when analysis related to a blood vessel is performed, the CT image data is produced back to projection data by a method such as a forward projection, and CT image data used in analysis is reconstructed, or reconstructed in an enlarged manner, from the projection data thus obtained.

Eleventh Modification of First Embodiment

The first embodiment and the modifications described above describe the example in which the medical image processing apparatus 100 displays a result of fluid analysis on the display 140 included in the apparatus, but the present embodiment is not limited thereto. For example, the medical image processing apparatus 100 may output an analysis result to a medical image display apparatus connected through the network 200.

Recently, a medical image processing system has been configured in some case as a thin client system in which a client apparatus used by the operator executes minimum necessary processing, and a server apparatus executes a large part of processing. For example, in such a medical image processing system, a processing circuitry included in the server apparatus may have a configuration similarly to that of the medical image processing apparatus 100 described in the first embodiment and the modifications described above, and the client apparatus (medical image display apparatus) may acquire, from the medical image processing apparatus 100, a result of analysis performed by the medical image processing apparatus 100, and display the result. For example, the client apparatus displays the analysis result through, for example, a general-purpose browser installed in the apparatus in advance.

Twelfth Modification of First Embodiment

The first embodiment and the modifications described above describe the example in which the CT image data collected by the X-ray CT apparatus 300 is used as image data related to the subject, but the present embodiment is not limited thereto. For example, image data collected by another medical image diagnostic apparatus may be used as the image data related to the subject. Examples of the medical image diagnostic apparatus include an MRI apparatus, an X-ray diagnostic apparatus, an ultrasonic diagnostic apparatus, and a PET apparatus.

Second Embodiment

The first embodiment and the modifications described above describe the example in which the medical image processing apparatus 100 executes various kinds of processing, but the present embodiment is not limited thereto. For example, the X-ray CT apparatus 300 may execute the various kinds of processing described above. The following describes this example as the second embodiment.

Figure 12:
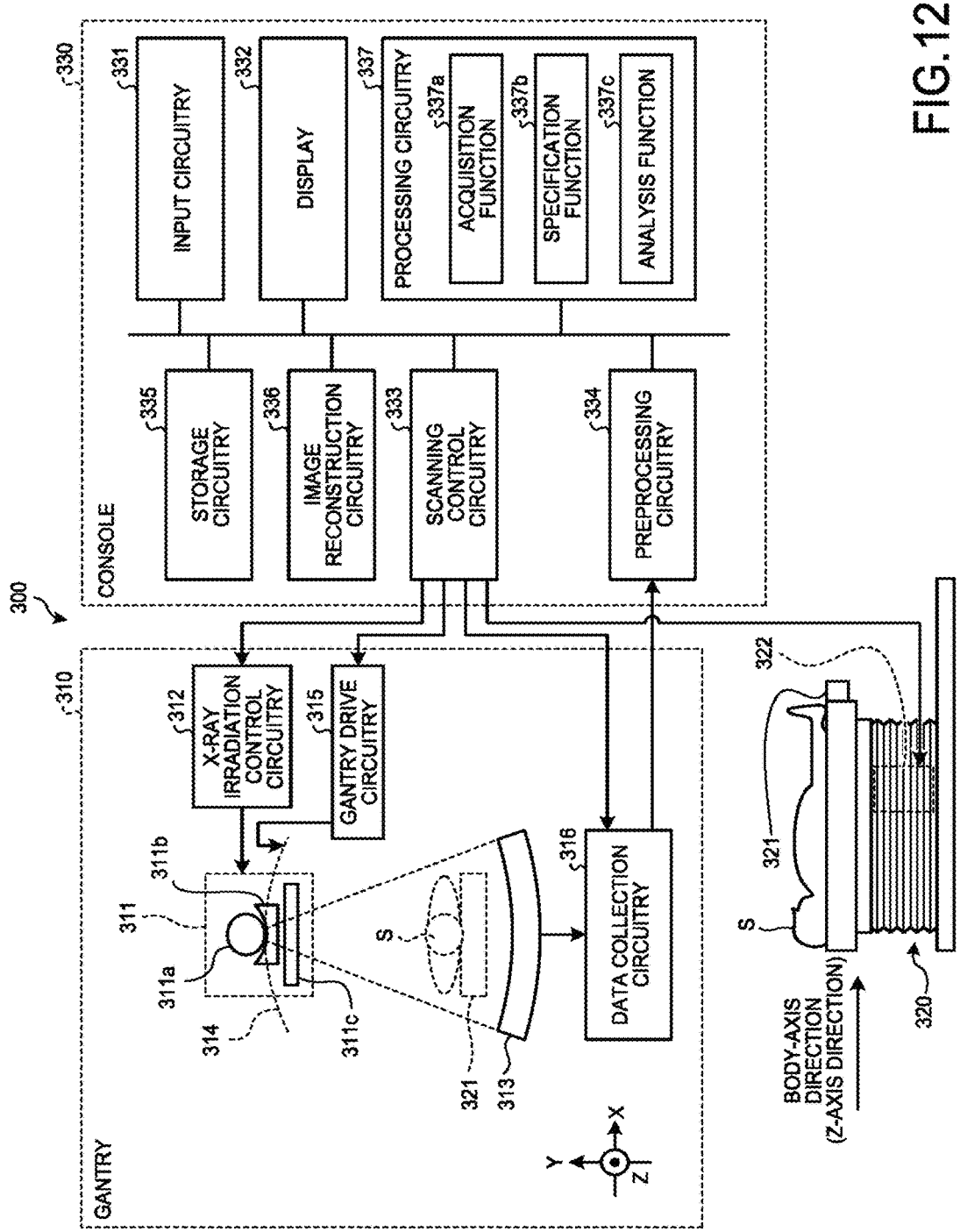
FIG. 12 is a diagram illustrating an exemplary configuration of an X-ray CT apparatus according to a second embodiment.

FIG. 12 is a diagram illustrating an exemplary configuration of the X-ray CT apparatus 300 according to the second embodiment. For example, as illustrated in FIG. 1, the X-ray CT apparatus 300 according to the present embodiment includes a gantry 310, a couch 320, and a console 330.

The gantry 310 is an apparatus configured to irradiate the subject S (patient) with X-ray, detect X-ray transmitted through the subject S, and output the detected X-ray to the console 330. For example, the gantry 310 includes an X-ray generation device 311, an X-ray irradiation control circuitry 312, a detector 313, a rotational frame 314, a gantry drive circuitry 315, and a data collection circuitry 316.

The X-ray generation device 311 generates X-ray and irradiates the subject S with the generated X-ray. For example, the X-ray generation device 311 includes an X-ray tube 311*a*, a wedge 311*b*, and a collimator 311*c*.

The X-ray tube 311*a* generates X-ray. For example, the X-ray tube 311*a* is a vacuum tube configured to generate X-ray with high voltage supplied from a high-voltage generation device not illustrated. The X-ray tube 311*a* generates X-ray spreading at a fan angle and a cone angle.

The wedge 311*b* is an X-ray filter for adjusting the amount of X-ray emitted from the X-ray tube 311*a*. Specifically, the wedge 311*b* is a filter configured to transmit and decay the X-ray emitted from the X-ray tube 311*a* so that the X-ray emitted from the X-ray tube 311*a* to the subject S has pre-defined distribution. For example, the wedge 311*b* is a filter fabricated from aluminum to have a pre-defined target angle and a pre-defined thickness. The wedge 311*b* is called a wedge filter or a bow-tie filter.

The collimator 311*c* is a slit for narrowing the range of irradiation with X-ray the amount of which is adjusted through the wedge 311*b* under control of the X-ray irradiation control circuitry 312 described later.

The X-ray irradiation control circuitry 312 controls the X-ray generation device 311 under control of a scanning control circuitry 333 described later. For example, the X-ray irradiation control circuitry 312 controls the high-voltage generation device not illustrated, so as to supply high voltage to the X-ray tube 311*a* included in the X-ray generation device 311. The X-ray irradiation control circuitry 312 adjusts the amount of X-ray incident on the subject S by adjusting a tube voltage and a tube current supplied to the X-ray tube 311*a*. The X-ray irradiation control circuitry 312 performs switching of the wedge 311*b* included in the X-ray generation device 311. The X-ray irradiation control circuitry 312 adjusts the range of irradiation (the fan angle and the cone angle) with X-ray by adjusting the opening degree of the collimator 311*c* included in the X-ray generation device 311.

The detector 313 detects X-ray generated from the X-ray tube 311*a*. For example, the detector 313 is a two-dimensional array detector (plane detector) configured to detect X-ray having transmitted through the subject S, in which a plurality of detection element lines each including arrangement of X-ray detection elements corresponding to a plurality of channels are arrayed in a body-axis direction (Z-axis direction illustrated in FIG. 1) of the subject S. Specifically, the detector 313 in the present embodiment includes X-ray detection elements arrayed as a large number of lines, for example, 320 lines in the body-axis direction of the subject S, and is capable of detecting X-ray having transmitted through a wide range of the subject S such as a range including the chest and the heart of the subject S.

The rotational frame 314 is formed in a circular ring, supporting the X-ray generation device 311 and the detector 313 such that the X-ray generation device 311 and the detector 313 are opposite to each other with respect to the subject S.

The gantry drive circuitry 315 rotates the rotational frame 314 under control of the scanning control circuitry 333 described later, thereby rotating the X-ray generation device 311 and the detector 313 on a circular orbit around the subject S at a center.

The data collection circuitry 316 collects, under control of the scanning control circuitry 333 described later, projection data from detection data of X-ray detected by the detector 313. The data collection circuitry 316 is also called a data acquisition system (DAS). For example, the data collection circuitry 316 generates projection data by performing, for example, amplification processing, A/D conversion processing, and inter-channel sensitivity correction processing on X-ray intensity distribution data detected by the detector 313, and transmit the generated projection data to the console 330 described later. The inter-channel sensitivity correction processing may be performed by a preprocessing circuitry 334 described later.

The couch 320 is an apparatus on which the subject S is placed, and includes a couchtop 321 on which the subject S is actually placed, and a couch drive device 322 as illustrated in FIG. 1. The couch drive device 322 moves the couchtop 321 in the Z-axis direction to move the subject S into the rotational frame 314.

The gantry 310 executes, for example, helical scanning that helically scans the subject S by rotating the rotational frame 314 while continuously moving the couchtop 321. Alternatively, the gantry 310 executes conventional scanning that scans the subject S on a circular orbit by rotating the rotational frame 314 while the position of the subject S is fixed after moving the couchtop 321. Alternatively, the gantry 310 executes a step and shoot scheme that performs the conventional scanning at a plurality of image pickup positions while moving the position of the couchtop 321 at a constant interval.

The console 330 is an apparatus configured to receive an operation of the X-ray CT apparatus 300 by the operator and reconstruct CT image data by using projection data collected by the gantry 310. As illustrated in FIG. 1, the console 330 includes an input circuitry 331, a display 332, the scanning control circuitry 333, the preprocessing circuitry 334, a storage circuitry 335, an image reconstruction circuitry 336, and a processing circuitry 337.

The input circuitry 331 includes a mouse, a keyboard, a track ball, a switch, a button, and a joystick, which are used by the operator of the X-ray CT apparatus 300 to input various instructions and various settings, and forwards, to the processing circuitry 337, information on instructions and settings received from the operator. For example, the input circuitry 331 receives, from the operator, for example, condition of image capturing of CT image data, condition of reconstructing CT image data, and condition of image processing on CT image data. The input circuitry 331 receives a specifying operation for specifying a site on an image, or a pre-defined region such as a region of interest.

The display 332 is a monitor referred to by the operator, and displays, under control of the processing circuitry 337, a CT image generated from CT image data to the operator, and a graphical user interface (GUI) for receiving, for example, various instructions and various settings from the operator through the input circuitry 331.

The scanning control circuitry 333 controls, under control of the processing circuitry 337, operation of the X-ray irradiation control circuitry 312, the gantry drive circuitry 315, the data collection circuitry 316, and the couch drive device 322, thereby controlling processing of collecting projection data at the gantry 310.

The preprocessing circuitry 334 generates corrected projection data by performing, on projection data generated by the data collection circuitry 316, logarithmic conversion processing, and correction processing such as offset correction, sensitivity correction, and beam hardening correction. Specifically, the preprocessing circuitry 334 generates corrected projection data from the protection data generated by the data collection circuitry 316, and stores the corrected projection data in the storage circuitry 335.

The storage circuitry 335 stores therein various kinds of data. For example, the storage circuitry 335 stores therein the projection data generated by the preprocessing circuitry 334, and CT image data generated by the image reconstruction circuitry 336 described later. The storage circuitry 335 stores therein various kinds of data generated as a result of processing executed by the processing circuitry 337 described later.

The image reconstruction circuitry 336 reconstructs CT image data by using the projection data stored by the storage circuitry 335. For example, the image reconstruction circuitry 336 reconstructs the CT image data by back projection processing using a filtered back projection (FBP) method or the like. Alternatively, for example, the image reconstruction circuitry 336 reconstructs the CT image data by using an iterative approximation method. The image reconstruction circuitry 336 generates various CT images by performing various kinds of image processing on the CT image data. Then, the image reconstruction circuitry 336 stores the reconstructed CT image data and the CT images generated by various kinds of image processing in the storage circuitry 335. The image reconstruction circuitry 336 is exemplary processing circuitry in the claims.

The processing circuitry 337 performs entire control of the X-ray CT apparatus 300 by controlling operation of the gantry 310, the couch 320, and the console 330. Specifically, the processing circuitry 337 controls CT scanning performed at the gantry 310 by controlling the scanning control circuitry 333. The processing circuitry 337 controls image reconstruction processing and image generation processing at the console 330 by controlling the image reconstruction circuitry 336. The processing circuitry 337 performs control to display various CT images stored in the storage circuitry 335 on the display 332.

With this configuration, in the X-ray CT apparatus 300 according to the present embodiment, the processing circuitry 337 includes an acquisition function 337a, a specification function 337b, and an analysis function 337c. The specification function 337b is exemplary processing circuitry in the claims.

The acquisition function 337a executes processing same as that executed by the acquisition function 151 described in the first embodiment and the modifications above. In the first embodiment and the modifications described above, the acquisition function 151 acquires CT image data or projection data from the X-ray CT apparatus 300 or the medical image storage apparatus 400. However, the acquisition function 337a according to the present embodiment acquires the CT image data or the projection data from the storage circuitry 335.

The specification function 337b executes processing same as that executed by the specification function 152 described in the first embodiment and the modifications above.

The analysis function 337c executes processing same as that executed by the analysis function 153 described in the first embodiment and the modifications above.

In the present embodiment, the input circuitry 331, the display 332, and the storage circuitry 335 have functions same as those of the input circuitry 130, the display 140, and the storage circuitry 120 described in the first embodiment above, respectively.

According to the second embodiment described above, similarly to the first embodiment, fluid analysis on the blood flow can be performed at a higher accuracy.

The embodiments described above describe the example in which each processing function is achieved by a single processing circuitry (the processing circuitry 150 or the processing circuitry 337), but the present embodiment is not limited thereto. For example, this processing circuitry may be configured as a combination of a plurality of independent processors, and each processor may achieve each processing function by executing the corresponding computer program. The processing functions included in this processing circuitry may be achieved through distribution or integration to a single or a plurality of processing circuitries as appropriate.

"Processor" used in the descriptions of the embodiments above refers to, for example, a central processing unit (CPU), a graphics processing unit (GPU), or a circuitry such as an application specific integrated circuit (ASIC) and a programmable logic device (for example, a simple programmable logic device (SPLD), a complex programmable logic device (CPLD), or a field programmable gate array (FPGA)). A computer program may be directly incorporated in the circuitry of such a processor instead of being stored in a storage circuitry. In this case, the processor achieves a function by reading and executing the computer program incorporated in the circuitry. Processors according to the present embodiment are not only configured as single circuitries, but may be configured as one processor as a combination of a plurality of independent circuitries to achieve their functions.

A computer program executed by the processors is incorporated and provided in, for example, a read-only memory (ROM) or a storage circuitry in advance. The computer program may be recorded and provided, as a file installable or executable at these processors, in a computer-readable storage medium such as a compact disc (CD)-ROM, a flexible disk (FD), a CD-R (Recordable), or a digital versatile disc (DVD). The computer program may be stored in a computer connected with a network such as the Internet, and provided or distributed by downloading through the network. For example, the computer program includes a module including each functional component described later. The computer program is read from a storage medium such as a ROM and executed by the CPU as actual hardware so as to load and generate the module on a main storage apparatus.

According to at least one of the embodiments described above, fluid analysis on the blood flow can be performed at a higher accuracy.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus, comprising:
processing circuitry configured to
acquire image data including image data of a coronary artery of a subject;
extract a region corresponding to the coronary artery from the image data;
obtain, by performing fluid analysis, a first index value related to a pressure of a blood flow flowing in the coronary artery as a first analysis result;
display the first analysis result;
obtain, by using a region of interest set based on the displayed first analysis result and performing fluid analysis based on a synthesis model, a second index value related to the pressure of the blood flow flowing in the coronary artery as a second analysis result, the synthesis model being obtained by coupling a first fluid analysis model corresponding to the region of interest and a second fluid analysis model corresponding to a region different from the region of interest, wherein an analysis accuracy of the second fluid analysis model is lower than that of the first fluid analysis model; and
display the second analysis result.

2. The medical image processing apparatus according to claim 1, wherein the region of interest is a region set by an operator while viewing the first analysis result.

3. The medical image processing apparatus according to claim 1, wherein the region of interest is a region in which the index value obtained as the first analysis result exceeds a threshold.

4. The medical image processing apparatus according to claim 1, wherein the region of interest is a region in which a vascular stenosis has occurred.

5. The medical image processing apparatus according to claim 1, wherein the processing circuitry is further configured to generate the first fluid analysis model of which analysis accuracy is higher than that of the second fluid analysis model by increasing resolution of image data as a basis of the first fluid analysis model.

6. The medical image processing apparatus according to claim 1, wherein the processing circuitry is further configured to generate the first fluid analysis model of which analysis accuracy is higher than that of the second fluid analysis model by increasing a calculation cost of fluid analysis using the first fluid analysis model.

7. The medical image processing apparatus according to claim 6, wherein the processing circuitry is further configured to perform the fluid analysis through simulation using a finite element method, and increase the calculation cost by increasing a density of a mesh in the first fluid analysis model.

8. The medical image processing apparatus according to claim 7, wherein the processing circuitry is further configured to generate the first fluid analysis model with the increased density of the mesh, and then compare the first fluid analysis model with the image data to correct the mesh.

9. The medical image processing apparatus according to claim 6, wherein the processing circuitry is further configured to increase the calculation cost through a change from one-dimensional analysis to three-dimensional analysis.

10. The medical image processing apparatus according to claim 6, wherein the processing circuitry is further configured to increase the calculation cost by increasing a convergence number of iterative calculation performed in the fluid analysis.

11. The medical image processing apparatus according to claim 1, wherein the processing circuitry is further configured to:
perform the fluid analysis for obtaining the first analysis result by using a fluid analysis model of the entire coronary artery;
generate, by using part of the fluid analysis model of the entire coronary artery corresponding to the region different from the region of interest as the second fluid analysis model, the synthesis model by coupling the first fluid analysis model and the second fluid analysis model; and perform the fluid analysis for obtaining the second analysis result by using the synthesis model.

12. The medical image processing apparatus according to claim 11, wherein, when generating the synthesis model, the processing circuitry is further configured to smoothly couple the first fluid analysis model and the second fluid analysis model by applying space interpolation in which the first fluid analysis model and the second fluid analysis model are coupled with each other.

13. The medical image processing apparatus according to claim 12, wherein, when performing fluid analysis using the synthesis model, the processing circuitry is further configured to omit calculation in the fluid analysis for a region positioned upstream of the region of interest among the region different from the region of interest by using an analysis result obtained by previously performed fluid analysis.

14. The medical image processing apparatus according to claim 1, wherein the processing circuitry is further configured to:

generate a fluid analysis model of which analysis accuracy is higher than that of the second fluid analysis model as the first fluid analysis model;

generate the synthesis model by coupling the first fluid analysis model and the second fluid analysis model; and perform the fluid analysis for obtaining the second analysis result by using the synthesis model.

15. The medical image processing apparatus according to claim 1, wherein the processing circuitry is further configured to set, as the region of interest, a region for which the first index value is out of a normal range.

16. The medical image processing apparatus according to claim 1, wherein the processing circuitry is further configured to perform an image correction on the image data, and then perform the fluid analysis by using the corrected image data.

17. The medical image processing apparatus according to claim 16, wherein the processing circuitry is further configured to perform, as the image correction, an image correction selected from a plurality of kinds of image corrections.

18. A medical image processing apparatus, comprising: processing circuitry configured to acquire image data including image data of a coronary artery of a subject;

extract a region corresponding to the coronary artery from the image data;

obtain, by performing fluid analysis, a first index value related to a pressure of a blood flow flowing in the coronary artery as a first analysis result;

display the first analysis result;

obtain, by using a region of interest set based on the displayed first analysis result and performing fluid analysis based on a synthesis model, a second index value related to the pressure of the blood flow flowing in the coronary artery as a second analysis result, the synthesis model being obtained by coupling a first fluid analysis model corresponding to the region of interest and a second fluid analysis model corresponding to a region different from the region of interest, wherein a mesh density or a spatial dimension of the second fluid analysis model is lower than that of the first fluid analysis model, and display the second analysis result.

19. A medical image processing method, comprising:

acquiring image data including image data of a coronary artery of a subject;

extracting a region corresponding to the coronary artery from the image data;

obtaining, by performing fluid analysis, a first index value related to a pressure of a blood flow flowing in the coronary artery as a first analysis result;

displaying the first analysis result;

obtaining, by using a region of interest set based on the displayed first analysis result and performing fluid analysis based on a synthesis model, a second index value related to the pressure of the blood flow flowing in the coronary artery as a second analysis result, the synthesis model being obtained by coupling a first fluid analysis model corresponding to the region of interest and a second fluid analysis model corresponding to a region different from the region of interest, wherein an analysis accuracy of the second fluid analysis model is lower than that of the first fluid analysis model, and displaying the second analysis result.

20. A medical image processing method, comprising:

acquiring image data including image data of a coronary artery of a subject;

extracting a region corresponding to the coronary artery from the image data;

obtaining, by performing fluid analysis, a first index value related to a pressure of a blood flow flowing in the coronary artery as a first analysis result;

displaying the first analysis result;

obtaining, by using a region of interest set based on the displayed first analysis result and performing fluid analysis based on a synthesis model, a second index value related to the pressure of the blood flow flowing in the coronary artery as a second analysis result, the synthesis model being obtained by coupling a first fluid analysis model corresponding to the region of interest and a second fluid analysis model corresponding to a region different from the region of interest, wherein a mesh density or a spatial dimension of the second fluid analysis model is lower than that of the first fluid analysis model, and displaying the second analysis result.

21. A medical image processing system, comprising:

a client apparatus including first processing circuitry; and a server apparatus including second processing circuitry, wherein the first processing circuitry is configured to transmit image data to the server apparatus, the image data including image data of a coronary artery of a subject, the second processing circuitry is configured to:

acquire the image data transmitted from the client apparatus;

extract a region corresponding to the coronary artery from the image data;

obtain, by performing fluid analysis, a first index value related to a pressure of a blood flow flowing in the coronary artery as a first analysis result; and transmit the first analysis result to the client apparatus, the first processing circuitry is further configured to:
  display the first analysis result transmitted from the server apparatus;
  set a region of interest based on the displayed first analysis result; and
  transmit the region of interest to the server apparatus,
the second processing circuitry is further configured to:
  obtain, by using the region of interest transmitted from the client apparatus and performing fluid analysis based on a synthesis model, a second index value related to the pressure of the blood flow flowing in the coronary artery as a second analysis result, the synthesis model being obtained by coupling a first fluid analysis model corresponding to the region of interest and a second fluid analysis model corresponding to a region different from the region of interest, wherein an analysis accuracy of the second fluid analysis model is lower than that of the first fluid analysis model; and
  transmit the second analysis result to the client apparatus, and
the first processing circuitry is further configured to display the second analysis result transmitted from the server apparatus.

22. A medical image processing system, comprising:
a client apparatus including first processing circuitry; and
a server apparatus including second processing circuitry, wherein
the first processing circuitry is configured to transmit image data to the server apparatus, the image data including image data of a coronary artery of a subject,
the second processing circuitry is configured to:
  acquire the image data transmitted from the client apparatus;
  extract a region corresponding to the coronary artery from the image data;
  obtain, by performing fluid analysis, a first index value related to a pressure of a blood flow flowing in the coronary artery as a first analysis result; and
  transmit the first analysis result to the client apparatus,
the first processing circuitry is further configured to:
  display the first analysis result transmitted from the server apparatus;
  set a region of interest based on the displayed first analysis result; and
  transmit the region of interest to the server apparatus,
the second processing circuitry is further configured to:
  obtain, by using the region of interest transmitted from the client apparatus and performing fluid analysis based on a synthesis model, a second index value related to the pressure of the blood flow flowing in the coronary artery as a second analysis result, the synthesis model being obtained by coupling a first fluid analysis model corresponding to the region of interest and a second fluid analysis model corresponding to a region different from the region of interest, wherein a mesh density or a spatial dimension of the second fluid analysis model is lower than that of the first fluid analysis model; and
  transmit the second analysis result to the client apparatus, and
the first processing circuitry is further configured to display the second analysis result transmitted from the server apparatus.

* * * * *